US010934470B2

(12) United States Patent
Lan et al.

(10) Patent No.: US 10,934,470 B2
(45) Date of Patent: Mar. 2, 2021

(54) HIGH TEMPERATURE HYDRATE INHIBITORS AND METHODS OF USE

(71) Applicant: Halliburton Energy Services, Inc., Houston, TX (US)

(72) Inventors: Qiang Lan, The Woodlands, TX (US); Deepak Monteiro, Houston, TX (US); Mark Paul Ceglio, II, El Paso, TX (US); Erick J. Acosta, Sugar Land, TX (US); Pushkala Krishnamurthy, Pearland, TX (US)

(73) Assignee: Multi-Chem Group, LLC, Houston, TX (US)

( * ) Notice: Subject to any disclaimer, the term of this patent is extended or adjusted under 35 U.S.C. 154(b) by 289 days.

(21) Appl. No.: 15/769,038

(22) PCT Filed: Dec. 18, 2015

(86) PCT No.: PCT/US2015/066824
§ 371 (c)(1),
(2) Date: Apr. 17, 2018

(87) PCT Pub. No.: WO2017/105507
PCT Pub. Date: Jun. 22, 2017

(65) Prior Publication Data
US 2020/0040249 A1    Feb. 6, 2020

(51) Int. Cl.
C09K 8/52        (2006.01)
C07C 233/36    (2006.01)
E21B 37/06     (2006.01)

(52) U.S. Cl.
CPC .............. C09K 8/52 (2013.01); C07C 233/36 (2013.01); E21B 37/06 (2013.01); *C09K 2208/22* (2013.01)

(58) Field of Classification Search
None
See application file for complete search history.

(56) References Cited

U.S. PATENT DOCUMENTS 5,648,575 A    7/1997  Klomp et al.
7,183,240 B2   2/2007  Dahlmann et al.
(Continued)

FOREIGN PATENT DOCUMENTS

WO    2010/104727 A1    9/2010
WO    2013/089802 A1    6/2013
(Continued)

OTHER PUBLICATIONS

International Search Report and Written Opinion issued in related PCT Application No. PCT/US2015/066824 dated Sep. 12, 2016, 12 pages.
(Continued)

*Primary Examiner* — John J Figueroa
(74) *Attorney, Agent, or Firm* — Tenley Krueger; Baker Botts L.L.P.

(57) ABSTRACT

Compositions and methods of using of such compositions to, for example, inhibit of the formation of gas hydrate agglomerates are provided. In one embodiment, the methods comprise: introducing a low-dosage hydrate inhibitor additive into a fluid, wherein the low-dosage hydrate inhibitor additive comprises a quaternary or tertiary ammonium cation moiety, a lipophilic tail, and a sulfonate anion moiety; and exposing the low-dosage hydrate inhibitor additive to a temperature above about 200° F.

17 Claims, 3 Drawing Sheets

(56) References Cited

U.S. PATENT DOCUMENTS

| | | |
|---|---|---|
| 7,381,689 B2 | 6/2008 | Panchalingam et al. |
| 8,134,011 B2 | 3/2012 | Rivers et al. |
| 8,329,620 B2 | 12/2012 | Acosta |
| 8,618,025 B2 | 12/2013 | Webber |
| 2005/0081432 A1* | 4/2005 | Panchalingam ......... C09K 8/52 44/419 |
| 2005/0261529 A1 | 11/2005 | Crosby et al. |
| 2006/0027369 A1* | 2/2006 | Baycroft ................. C09K 8/52 166/300 |
| 2008/0064611 A1 | 3/2008 | Spratt |
| 2012/0078021 A1 | 3/2012 | Durhan et al. |

FOREIGN PATENT DOCUMENTS

| | | |
|---|---|---|
| WO | 2014/052940 A1 | 4/2014 |
| WO | WO-2015051137 A1 * | 4/2015 ............. C09K 8/524 |

OTHER PUBLICATIONS

International Preliminary Report on Patentability issued in related PCT Application No. PCT/US2015/066824 dated Jun. 28, 2018, 9 pages.

* cited by examiner

HIGH TEMPERATURE HYDRATE INHIBITORS AND METHODS OF USE

CROSS-REFERENCE TO RELATED APPLICATION

The present application is a U.S. National Stage Application of International Application No. PCT/US2015/066824 filed Dec. 18, 2015, which is incorporated herein by reference in its entirety for all purposes.

BACKGROUND

The present disclosure relates to compositions and methods useful in processes involving fluid flowing through, or contained in, conduits, such as pipes used, e.g., for the production and/or transport of petroleum products, natural gas, and the like.

Gas hydrates are solids that may agglomerate in a fluid that is flowing or is substantially stationary, under certain temperature and pressure conditions. For example, gas hydrates may form during hydrocarbon production from a subterranean formation, in particular in pipelines and other equipment during production operations. Hydrates may impede or completely block flow of hydrocarbons or other fluid flowing through such pipelines. These blockages not only may decrease or stop production, potentially costing millions of dollars in lost production, but also may be very difficult and dangerous to mediate. Unless properly handled, gas hydrates may be volatile and/or explosive, potentially rupturing pipelines, damaging equipment, endangering workers, and/or causing environmental harm.

Gas hydrates may form when water molecules become bonded together after coming into contact with certain "guest" gas or liquid molecules. Hydrogen bonding causes the water molecules to form a regular lattice structure, like a cage, that is stabilized by the guest gas or liquid molecules entrapped within the lattice structure. The resulting crystalline structure may precipitate as a solid gas hydrate. Guest molecules can include any number of molecules such as, for example, carbon dioxide, methane, butane, propane, hydrogen, helium, freon, halogen, noble gases, and the like.

BRIEF DESCRIPTION OF THE DRAWINGS

These drawings illustrate certain aspects of some of the embodiments of the present disclosure and should not be used to limit or define the claims.

Figure 1:
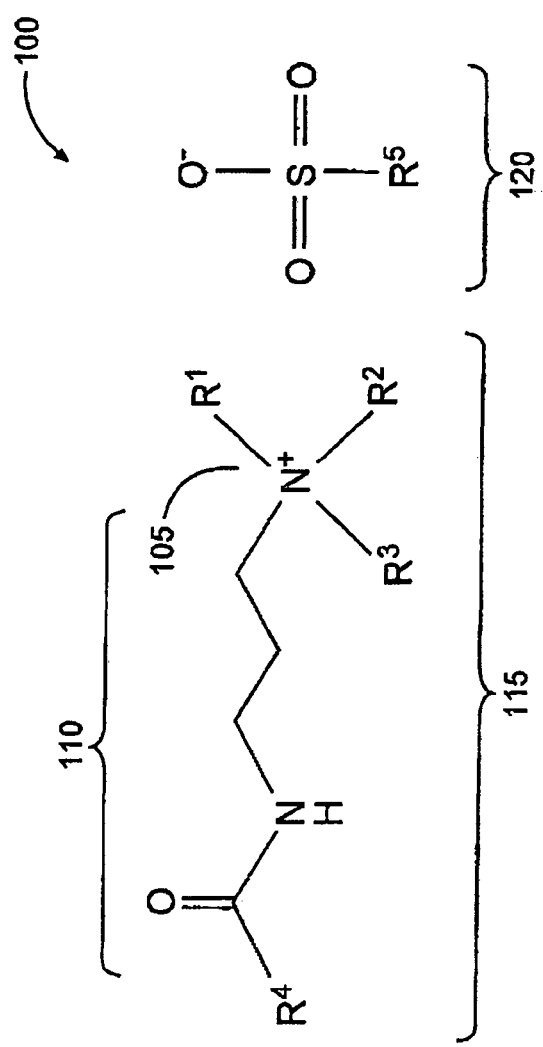
FIG. 1 is a diagram illustrating a low-dosage hydrate inhibitor additive in accordance with certain embodiments of the present disclosure.

While embodiments of this disclosure have been depicted, such embodiments do not imply a limitation on the disclosure, and no such limitation should be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DESCRIPTION OF CERTAIN EMBODIMENTS

Illustrative embodiments of the present disclosure are described in detail herein. In the interest of clarity, not all features of an actual implementation may be described in this specification. It will of course be appreciated that in the development of any such actual embodiment, numerous implementation-specific decisions may be made to achieve the specific implementation goals, which may vary from one implementation to another. Moreover, it will be appreciated that such a development effort might be complex and time-consuming, but would nevertheless be a routine undertaking for those of ordinary skill in the art having the benefit of the present disclosure.

To facilitate a better understanding of the present disclosure, the following examples of certain embodiments are given. In no way should the following examples be read to limit, or define, the scope of the invention. Embodiments of the present disclosure involving wellbores may be applicable to horizontal, vertical, deviated, or otherwise nonlinear wellbores in any type of subterranean formation. Embodiments may be applicable to injection wells, monitoring wells, and production wells, including hydrocarbon or geothermal wells.

Hydrate inhibitors are often grouped into 3 general classes: thermodynamic, anti-agglomerate, and kinetic hydrate inhibitors. Thermodynamic inhibitors are believed to operate by shifting the hydrate formation phase boundary away from temperature and pressure conditions of a process by increasing the driving force required for formation of the hydrate. Kinetic hydrate inhibitors may prevent or delay the nucleation of hydrates, thus limiting hydrate crystal size and growth. Anti-agglomerate inhibitors are believed to prevent or otherwise disrupt the agglomeration of hydrates. Thermodynamic inhibitors may require high concentrations to be effective. Kinetic inhibitors and anti-agglomerate inhibitors may function at lower concentrations than thermodynamic inhibitors, and therefore may be termed low-dosage hydrate inhibitors (LDHIs).

The present disclosure relates to compositions and methods useful in processes involving fluid flowing through, or contained in, conduits, such as pipes used, e.g., for the production and/or transport of petroleum products, natural gas, and the like. More particularly, the present disclosure relates to LDHI additives and method of using such LDHI additives to, for example, inhibit the formation of gas hydrate agglomerates.

In certain embodiments, the present disclosure may provide a LDHI additive comprising a lipophilic tail, a hydrophilic head, and a linking moiety. In some embodiments, the LDHI additive may be provided, used, and/or introduced as a salt. In certain embodiments, the present disclosure further provides methods of using such LDHI additives to inhibit the formation of one or more hydrates in a fluid. For example, certain embodiments of the present disclosure provide methods of adding one or more LDHI additives of the present disclosure to a fluid comprising any one or more of water, a gas, a liquid hydrocarbon, and any combination thereof. In certain embodiments, such a method may include adding to the fluid an effective amount of a LDHI additive of the present disclosure to inhibit, retard, reduce, control, delay, and/or the like the formation of hydrate agglomerates.

Among the many advantages to the compositions and methods of the present disclosure, only some of which are alluded to herein, the LDHI additives and methods of the present disclosure may, among other benefits, provide for enhanced anti-agglomeration properties and/or enhanced inhibition, retardation, mitigation, reduction, control, delay, and/or the like of agglomeration of hydrates and/or hydrate-forming compounds. In certain embodiments, agglomeration of hydrates and/or hydrate-forming compounds may be inhibited (and the like) to a greater degree than that achieved using other hydrate inhibition means. In certain embodiments, a smaller quantity of the LDHI additives of the present disclosure may achieve the same degree of inhibition of agglomeration of hydrates and/or hydrate-forming compounds as a greater amount of other LDHIs. In certain embodiments, the LDHI additives and methods of the present disclosure may inhibit agglomeration of hydrates and/or hydrate-forming compounds to a greater degree in fluids comprising salt water in an amount above about 60% by total volume of the water in the fluid and/or fluids comprising deionized water in an amount above 10% by total volume of the water in the fluid than other LDHIs.

In certain embodiments, the LDHI additives of the present disclosure may at least partially inhibit, retard, reduce, control, and/or delay the agglomeration of hydrates and/or hydrate-forming compounds during and/or after exposure to high temperatures. In such embodiments, the LDHI additives of the present disclosure may not substantially degrade after an extended period of time at such high temperatures. As used herein, "substantially" and variations of that term may refer to a majority of, or mostly, as in at least about 50%, 60%, 70%, 80%, 90%, 95%, 96%, 97%, 98%, 99%, 99.5%, 99.9%, 99.99%, or at least about 99.999% or more. In certain embodiments, the LDHI additives of the present disclosure may be substantially or completely free of halogens, which may allow for processing of fluids, such as refining, comprising the LDHI additives of the present disclosure in facilities without the need to remove halogens from the fluids. Additionally, it is believed that the LDHI additives of the present disclosure may provide benefits and/or may be used as an additive for purposes other than hydrate inhibition, such as, for example, corrosion inhibition.

The LDHI additives of the present disclosure may comprise a hydrophilic head comprising a cation moiety that may be a quaternary ammonium cation moiety or a tertiary ammonium cation moiety. FIG. 1 illustrates the chemical structure for certain LDHI additives of the present disclosure. In certain embodiments, the cation moiety in the LDHI additives of the present disclosure may be bonded to other moieties of the LDHI additive, for example, as shown with respect to the hydrophilic head 105 of the LDHI additive 100 in FIG. 1. In certain embodiments, the cation moiety may be substantially of the composition —$R^1R^2R^3N^+$—. Each of $R^1$, $R^2$, and $R^3$ may independently comprise either a hydrogen atom or a $C_1$ to $C_6$ hydrocarbon chain. As used herein, a "hydrocarbon chain" may, unless otherwise specifically noted, be branched, unbranched, non-cyclic, and/or cyclic; it may be substituted or unsubstituted (that is, it may or may not contain one or more additional moieties or functional groups in place of one or more hydrogen atoms in the hydrocarbon chain); and/or it may be saturated or unsaturated. Furthermore, as used herein, the nomenclature "$C_x$ to $C_y$" refers to the number of carbon atoms in the hydrocarbon chain (here, ranging from x to y carbon atoms).

In certain embodiments, $R^1$, $R^2$, and/or $R^3$ may be a hydrogen atom. In certain embodiments, only one of $R^1$, $R^2$, and $R^3$ may be a hydrogen atom. In those embodiments, the cation moiety is a tertiary ammonium cation moiety. In such embodiments wherein $R^1$, $R^2$, and/or $R^3$ comprises a $C_1$ to $C_6$ hydrocarbon chain, the hydrocarbon chain may comprise any one or more hydrocarbon groups selected from the group consisting of: alkyl, alkenyl, alkynyl, aryl, arylalkyl, arylalkenyl, alkylaryl, alkenylaryl, and any combination thereof. In such embodiments, any one or more of $R^1$, $R^2$, and $R^3$ may be branched, unbranched, non-cyclic, cyclic, saturated, and/or unsaturated. In certain embodiments, each of $R^1$, $R^2$, and $R^3$ may independently comprise (i) as few as any one of: 1, 2, 3, 4, 5, and 6 carbon atoms, and (ii) as many as one of: 4, 5, and 6 carbon atoms. For example, suitable ranges of carbon atoms in each of $R^1$, $R^2$, and $R^3$ according to various embodiments of the present disclosure include, but are not limited to, 1 to 2, 1 to 3, 1 to 4, 1 to 5, 1 to 6, 2 to 4, 3 to 5, and 4 to 6, and the like.

In some embodiments, any one or more of $R^1$, $R^2$, and $R^3$ may comprise a $C_1$ to $C_6$ alkyl chain. In some embodiments, any one or more of $R^1$, $R^2$, and $R^3$ may comprise a $C_2$ to $C_6$ alkenyl or alkynyl chain (in which case at least 2 carbon atoms are necessary to form an alkenyl or alkynyl chain). In some embodiments, any one or more of $R^1$, $R^2$, and $R^3$ may comprise a $C_3$ to $C_6$ cyclic moiety (in which case at least 3 carbon atoms are necessary to form a cyclic moiety). In certain embodiments, any one or more of $R^1$, $R^2$, and $R^3$ may be substituted (e.g., it may include any one or more functional groups in addition to the hydrocarbon groups described above), so long as the cation moiety remains hydrophilic.

The LDHI additives of the present disclosure may further comprise a lipophilic tail. For example, as shown in FIG. 1, the LDHI additive 100 comprises a lipophilic tail $R^4$. In certain embodiments, the lipophilic tail of the LDHI additives of the present disclosure may comprise a $C_1$ to $C_{50}$ hydrocarbon chain. In certain embodiments, the hydrocarbon chain on the lipophilic tail may be branched or unbranched, cyclic or non-cyclic, saturated or saturated, and/or may be any one or more of alkyl, alkenyl, alkynyl, and aryl groups, and/or any combination thereof. In certain embodiments, the lipophilic tail may further optionally be substituted with any one or more functional groups, so long as such substituted functional group(s) do not alter the lipophilic and/or hydrophobic nature of the lipophilic tail. In certain embodiments, the lipophilic tail may comprise (i) as few as any one of: 1, 2, 3, 4, 5, 6, 7, 8, 9, 10, 11, 12, 13, 14, 15, 16, 17, 18, 19, and 20 carbon atoms, and (ii) as many as any one of: 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, and 50 carbon atoms. For example, suitable ranges of carbon atoms in the lipophilic tail according to various embodiments of the present disclosure include, but are not limited to, 1 to 5, 3 to 5, 4 to 8, 5 to 15, 8 to 18, 12 to 16, 8 to 20, 10 to 20, 15 to 20, and the like. It will be appreciated by one of ordinary skill in the art having the benefit of the present disclosure that even in such embodiments, additional lipophilic tails could be included in the LDHI additive (e.g., at a point along the backbone 115 of the LDHI additive 100).

The LDHI additives of the present disclosure may further comprise a linking moiety. As used herein, "linking moiety" refers to any portion of the LDHI additive that provides spacing between the hydrophilic head and the lipophilic tail. In certain embodiments, the lipophilic tail may be connected to the hydrophilic head via the linking moiety. For example, in the LDHI additive 100 shown in FIG. 1 the lipophilic tail $R^4$ is connected to the hydrophilic head 105 via the linking moiety 110. In certain embodiments, the linking moiety may provide sufficient spacing so that the LDHI additive maintains an overall substantially amphiphilic character.

In certain embodiments, the linking moiety may comprise any length hydrocarbon chain, branched or unbranched, and/or saturated or unsaturated (so long as the overall LDHI additive maintains amphiphilic character). Hydrocarbon chain lengths include $C_1$ to $C_{50}$ chains or longer. In certain embodiments, the linking moiety may be any one or more of methyl, ethyl, propyl, butyl, pentyl, hexyl, heptyl, octyl, nonyl, decyl, etc. In certain embodiments, the linking moiety may be substituted such that it includes any kind and any number of functional groups (so long as the LDHI additive maintains both hydrophobic and hydrophilic portions). In such embodiments, the one or more functional groups that may be included on the linking moiety according to some embodiments should not adversely affect the hydrophilic nature of a hydrophilic head, nor should they adversely affect the lipophilic nature of a lipophilic tail. Examples of suitable functional groups that may be included in the linking moieties, the lipophilic tails, and/or the R-groups ($R^1$, $R^2$, $R^3$) of the present disclosure may include any one or more of: an ester, ether, amine, sulfonamide, amide, ketone, carbonyl, isocyanate, urea, urethane, and any combination thereof. In some embodiments, the one or more functional groups on the linking moiety may include any group capable of reacting with an amine (so long as that functional group's inclusion in the linking moiety allows the LDHI additive to maintain amphiphilic character). The LDHI additive 100 of FIG. 1 includes an example of a linking moiety 110 comprising an amide as well as a propyl group.

The LDHI additives of the present disclosure may instead or in addition be characterized as reaction products. For instance, in some embodiments, the present disclosure provides LDHI additives that may be characterized as the reaction product of: (1) dialkylaminopropylamine and (2) one or more fatty acids or fatty acid esters. In such embodiments, the two alkyl groups (i.e., dialkyl) may be either the same or different, and $R^1$ and $R^2$ of the cation moiety may depend upon the identity of the two alkyl group(s). In some embodiments, the reaction product of (1) dialkylaminopropylamine and (2) one or more fatty acids or fatty acid esters may further be reacted with (3) an alkyl sulfonate or dialkyl sulfate. In such embodiments, $R^3$ of the cation moiety may depend upon the alkyl group of the alkyl sulfonate or dialkyl sulfate. In certain embodiments, the composition of the lipophilic tail of the LDHI additive may depend upon the fatty acid(s) and/or fatty acid ester(s) used as reactant(s). In certain embodiments, the fatty acid and/or fatty acid ester may comprise one or more functional groups and a portion of the functional group may be included in the linking moiety of the resultant reactant product. Suitable fatty acids and/or fatty acid esters for reaction may include a saturated fatty acid and/or an unsaturated fatty acid, such as one or more selected from the group consisting of: corn oil, canola oil, coconut oil, safflower oil, sesame oil, palm oil, cottonseed oil, soybean oil, olive oil, sunflower oil, hemp oil, wheat germ oil, palm kernel oil, vegetable oil, caprylic acid, capric acid, lauric acid, stearic acid, myristic acid, myristoleic acid, palmitic acid, palmitoleic acid, stearic acid, sapienic acid, elaidic acid, vaccenic acid, linoleic acid, arachidic acid, arachidonic acid, eicosapentaenoic acid, erucic acid, docosahexaenoic acid, behenic acid, lignoceric acid, cerotic acid, oleic acids (cis- and trans-), any fatty acid derived therefrom, and any combination thereof.

Figure 2:
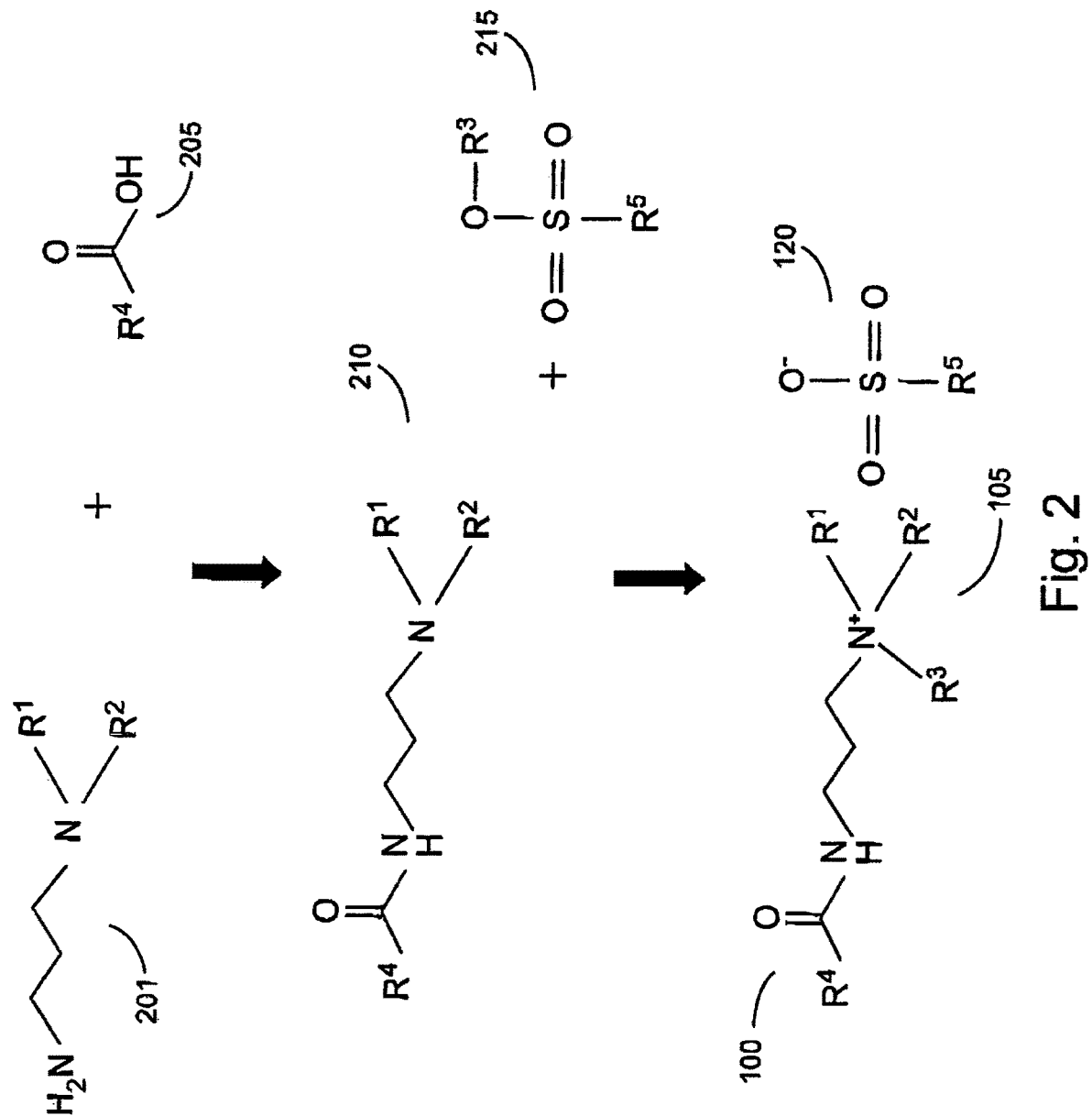
FIG. 2 is a diagram illustrating an example reaction process in accordance with certain embodiments of the present disclosure.

FIG. 2 illustrates a potential reaction scheme for forming a LDHI additive (and its formation) in accordance with certain embodiments of the present disclosure. In the reaction scheme shown, dialkylaminopropylamine 201 (which, as shown in FIG. 2, comprises hydrocarbon chains $R^1$ and $R^2$) reacts with fatty acid ester 205 (which, as shown in FIG. 2, comprises hydrocarbon chain $R^4$), forming amide intermediate 210. Amide intermediate 210 in turn reacts with alkyl sulfonate 215 (which, as shown in FIG. 2, comprises hydrocarbon chain $R^3$ and organic moiety $R^5$) to form LDHI additive 100. As can be seen, LDHI additive 100 includes a lipophilic tail $R^4$ (retaining the hydrocarbon structure $R^4$ of the fatty acid ester 205) and a hydrophilic head 105 comprising a R-groups $R^1$ and $R^2$ (retaining the hydrocarbon structure $R^1$ and $R^2$ of the dialkylaminopropylamine 201) and $R^3$ (retaining the hydrocarbon structure $R^3$ of the alkyl sulfonate 215). Such reactions may in some embodiments take place at about 80° C. to about 250° C. at approximately atmospheric pressure or lower pressure. It will be appreciated by one of ordinary skill in the art having the benefit of the present disclosure that various modifications may be made to this reaction scheme to produce other embodiments. Furthermore, in yet other embodiments, another reactant besides fatty acids may be used. Examples of suitable other reactants include, but are not limited to, esters, sulfonamides, amides, ketones, carbonyls, isocyanates, urea, urethane, and any combination thereof.

In certain embodiments, the LDHI additives of the present disclosure may be provided, used, and/or introduced as a salt of one or more of the compounds described herein. In such embodiments, the salt may comprise a counter anion. For example, the LDHI additive 100 as shown in FIGS. 1 and 2 comprise a salt with a sulfate counter anion 120. In certain embodiments, such salts may wholly or partially dissociate in aqueous solution. In other embodiments, the salts may remain substantially associated (either with the original anion or with other ions from solution). It will be appreciated by one of ordinary skill in the art having the benefit of this disclosure that salts may be formed with other counter anions instead of or in addition to sulfate counter anions. Suitable counter anions may comprise, for example, any one or more of hydroxide, carboxylate, halide, sulfate, organic sulfonate, and any combination thereof. In certain embodiments, such counter anions may comprise an organic moiety. For example, the counter anion 120 of FIG. 1 comprises organic moiety $R^5$. Suitable organic moieties may comprise, for example, a hydrocarbon chain, such as an alkyl, alkenyl, aryl, arylalkyl, arylalkenyl, alkylaryl, or alkenylaryl group, a heterocyclic group, a hydroxyl group, a carbonyl group, an amine group, and any combination thereof.

In certain embodiments, the LDHI additives of the present disclosure may have substantially the following structural formula:

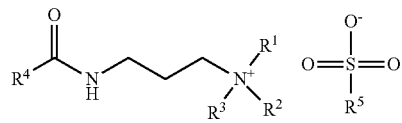

In such embodiments, each of $R^1$ and $R^2$ may independently be a $C_1$ to $C_6$ hydrocarbon chain according to the previous discussion of the $R^1$ and $R^2$ groups; $R^3$ may be selected from the group consisting of hydrogen and a $C_1$ to $C_6$ hydrocarbon chain according to the previous discussion of the $R^3$ group; $R^4$ may be a $C_1$ to $C_{50}$ hydrocarbon chain according to the previous discussion of the $R^4$ group; and $R^5$ may be an organic moiety according to the previous discussion of the $R^5$ group.

The present disclosure in certain embodiments further provides methods of using the LDHI additives of the present disclosure. In certain embodiments, the LDHI additives of the present disclosure may be used to inhibit, retard, mitigate, reduce, control, and/or delay the formation of one or more hydrates or agglomerates of hydrates. In certain embodiments, one or more LDHI additives of the present disclosure may be introduced into a fluid comprising any one or more of water, a gas, a liquid hydrocarbon, and any combination thereof. Although listed separately from liquid hydrocarbon, the gas may in some embodiments include gaseous hydrocarbon, though the gas need not necessarily include hydrocarbon. In certain embodiments, the LDHI additive may be introduced into the fluid through a conduit or an injection point. In certain embodiments, one or more LDHI additives of the present disclosure may be introduced into a wellbore, a conduit, a vessel, and the like and may contact and/or be introduced into a fluid residing therein.

In certain embodiments, the fluid may be flowing or it may be substantially stationary. The fluid may be within a vessel, or within a conduit (e.g., a conduit that may transport the fluid), or within a subterranean formation and/or a wellbore penetrating a portion of the subterranean formation. Examples of conduits include, but are not limited to, pipelines, production piping, subsea tubulars, process equipment, and the like as used in industrial settings and/or as used in the production of oil and/or gas from a subterranean formation, and the like. The conduit may in certain embodiments penetrate at least a portion of a subterranean formation, as in the case of an oil and/or gas well. In particular embodiments, the conduit may be a wellbore or may be located within a wellbore penetrating at least a portion of a subterranean formation. Such oil and/or gas well may, for example, be a subsea well (e.g., with the subterranean formation being located below the sea floor), or it may be a surface well (e.g., with the subterranean formation being located belowground). A vessel or conduit according to other embodiments may be located in an industrial setting such as a refinery (e.g., separation vessels, dehydration units, pipelines, heat exchangers, and the like), or it may be a transportation pipeline.

In some embodiments, the LDHI additives of the present disclosure initially may be incorporated into a composition prior to be introduced into the fluid. The composition may be any suitable composition in which the LDHI additive may be included. For example, in some embodiments, the composition may be a treatment fluid for use in a wellbore penetrating a subterranean formation during, for instance, oil and/or gas recovery operations. The composition may include a solvent for the LDHI additive. Suitable solvents include any one or more of: toluene, xylene, methanol, isopropyl alcohol, any alcohol, glycol, any organic solvent, and any combination thereof.

In certain embodiments, one or more LDHI additives of the present disclosure may be introduced into and/or contact the fluid in an amount from about 0.1% to about 5.5% by volume based on the volume of water in the fluid (or in other words, about 0.1% to about 5.5% by volume based on water cut). In various embodiments, an effective amount of LDHI additive for inhibiting, retarding, mitigating, reducing, controlling, delaying, and/or the like agglomeration of hydrates may be as low as any of: 0.1, 0.25, 0.50, 0.75, 1.00, 1.25, 1.50, 1.75, 2.00, 2.25, and 2.50% by volume based on water cut. An effective amount may be as high as any of: 0.50, 0.75, 1.0, 1.25, 1.50, 1.75, 2.0, 2.25, 2.50, 2.75, 3.0, 3.25, 3.50, 3.75, 4.0, 4.50, 5.0, and 5.50% by volume based on water cut. Thus, in some embodiments, an effective amount of LDHI additives of the present disclosure for inhibiting, retarding, mitigating, reducing, controlling, delaying, and/or the like agglomeration of hydrates may be about 0.1% to about 3% volume based on water cut of the fluid; in other embodiments, about 0.1% to about 2% volume based on water cut of the fluid; in other embodiments, about 0.25% to about 1.5% volume based on water cut of the fluid; and in other embodiments, about 0.5% to about 1.0% volume based on water cut of the fluid.

In certain embodiments, one or more LDHI additives of the present disclosure may be introduced to and/or contact any of various fluids having different water cuts (i.e., the ratio of the volume of water in the fluid to the total volume of the fluid). For example, in some embodiments the water cut of the fluid may be about 1 to about 65%. In other embodiments, the water cut may be as low as any one of: 1, 5, 10, 15, 20, 25, 30, 35, 40, 45, 50, 55, 60, and 65%; while the water cut may be as high as any one of: 5, 10, 15, 20, 25, 30, 35, 40, 45, 50, 55, 60, 65, 70, 75, 80, 85, 90, and 95%. In certain embodiments, a fluid may have a water cut of 5% or more, 10% or more, 15% or more, 20% or more, 30% or more, 40% or more, 50% or more, or 60% or more, up to about 99%. In yet other embodiments, one or more LDHI additives of the present disclosure may be introduced into or contact a fluid with any water cut ranging from about 1% to about 99%.

In certain embodiments, the fluid to which one or more LDHI additives of the present disclosure may be introduced optionally may comprise any number of additional additives. Examples of such additional additives include, but are not limited to, salts, surfactants, acids, proppant particulates, diverting agents, fluid loss control additives, nitrogen, carbon dioxide, surface modifying agents, tackifying agents, foamers, corrosion inhibitors, scale inhibitors, catalysts, clay control agents, biocides, friction reducers, antifoam agents, bridging agents, flocculants, $H_2S$ scavengers, $CO_2$ scavengers, oxygen scavengers, lubricants, viscosifiers, breakers, weighting agents, relative permeability modifiers, resins, wetting agents, coating enhancement agents, filter cake removal agents, antifreeze agents (e.g., ethylene glycol), and the like. A person skilled in the art, with the benefit of this disclosure, will recognize the types of additives that may be included in the fluids of the present disclosure for a particular application. It further will be appreciated by one of ordinary skill in the art having the benefit of the present disclosure that the amount of the LDHI additives of the present disclosure effective for inhibiting, retarding, reducing, controlling, delaying, and/or the like hydrates may depend upon, for example, the volume of water in the fluid and/or additives in the fluid.

In certain embodiments, the LDHI additives of the present disclosure may be exposed to a temperature above about 200° F. In certain embodiments, LDHI additives of the present disclosure may be exposed to a temperature from about 200° F. to about 400° F. In some embodiments, the LDHI additives of the present disclosure may be exposed to a temperature from about 200° F. to about 250° F., in other embodiments, from about 250° F. to about 300° F., in other embodiments, from about 300° F. to about 350° F., and in other embodiments, from about 350° F. to about 400° F. In some embodiments, the LDHI additives of the present disclosure may be exposed to a temperature from about 250° F. to about 275° F., in other embodiments, from 275° F. to about 300° F., in other embodiments, from about 300° F. to about 325° F., and in other embodiments from about 325° F. to about 350° F.

In certain embodiments, the LDHI additives may be exposed to a temperature of above about 200° F. when introduced into or contacting a fluid having a temperature of above about 200° F. In such embodiments, the fluid may have a temperature from about 200° F. to about 400° F. In some embodiments, the fluid may have a temperature from about 250° F. to about 350° F. In certain embodiments, the LDHI additive may be exposed to a temperature above about 200° F. in a conduit, an injection point, a wellbore, and the like having a temperature above about 200° F. through which the LDHI additive travels when being introduced into or contacting the fluid.

In certain embodiments, the LDHI additives of the present disclosure may be exposed to a temperature above about 200° F. for an extended period of time without substantially degrading. In certain embodiments, the LDHI additives of the present disclose may remain in a fluid having a temperature above 200° F. for an extended period of time without substantially degrading. In some embodiments, the LDHI additives of the present disclosure may be exposed to a temperature above about 200° F., alternatively above about 250° F., alternatively above 300° F., alternatively above about 350° F., or alternatively above about 400° F. for an extended period of time without substantially degrading. In some embodiments, the LDHI additives of the present disclosure may be exposed to a temperature above about 200° F. without substantially degrading for up to about: 1, 2, 3, 4, 5, 6, 7 or more days. In certain embodiments, the LDHI additives of the present disclosure do not substantially degrade after about 7 days at a temperature above about 200° F.

In certain embodiments, the LDHI additives of the present disclosure may be introduced into a wellbore, subterranean formation, vessel, and/or conduit (and/or into a fluid within any of the foregoing) using any method or equipment known in the art. For example, the LDHI additives of the present disclosure may be applied to a subterranean formation and/or wellbore using batch treatments, squeeze treatments, continuous treatments, and/or any combination thereof. In certain embodiments, a batch treatment may be performed in a subterranean formation by stopping production from the well and pumping the dissolved hydrate inhibitors into a wellbore, which may be performed at one or more points in time during the life of a well. In other embodiments, a squeeze treatment may be performed by dissolving a LDHI additive of the present disclosure in a suitable solvent at a suitable concentration and squeezing that solvent carrying the hydrate inhibitor downhole into the formation, allowing production out of the formation to bring the hydrate inhibitor to its desired location. In other embodiments, a LDHI additive of the present disclosure may be injected into a portion of a subterranean formation using an annular space or capillary injection system to continuously introduce the LDHI additive into the formation. In certain embodiments, a composition (such as a treatment fluid) comprising a LDHI additive of the present disclosure may be circulated in the wellbore using the same types of pumping systems and equipment at the surface that are used to introduce treatment fluids or additives into a wellbore penetrating at least a portion of the subterranean formation.

Figure 3:
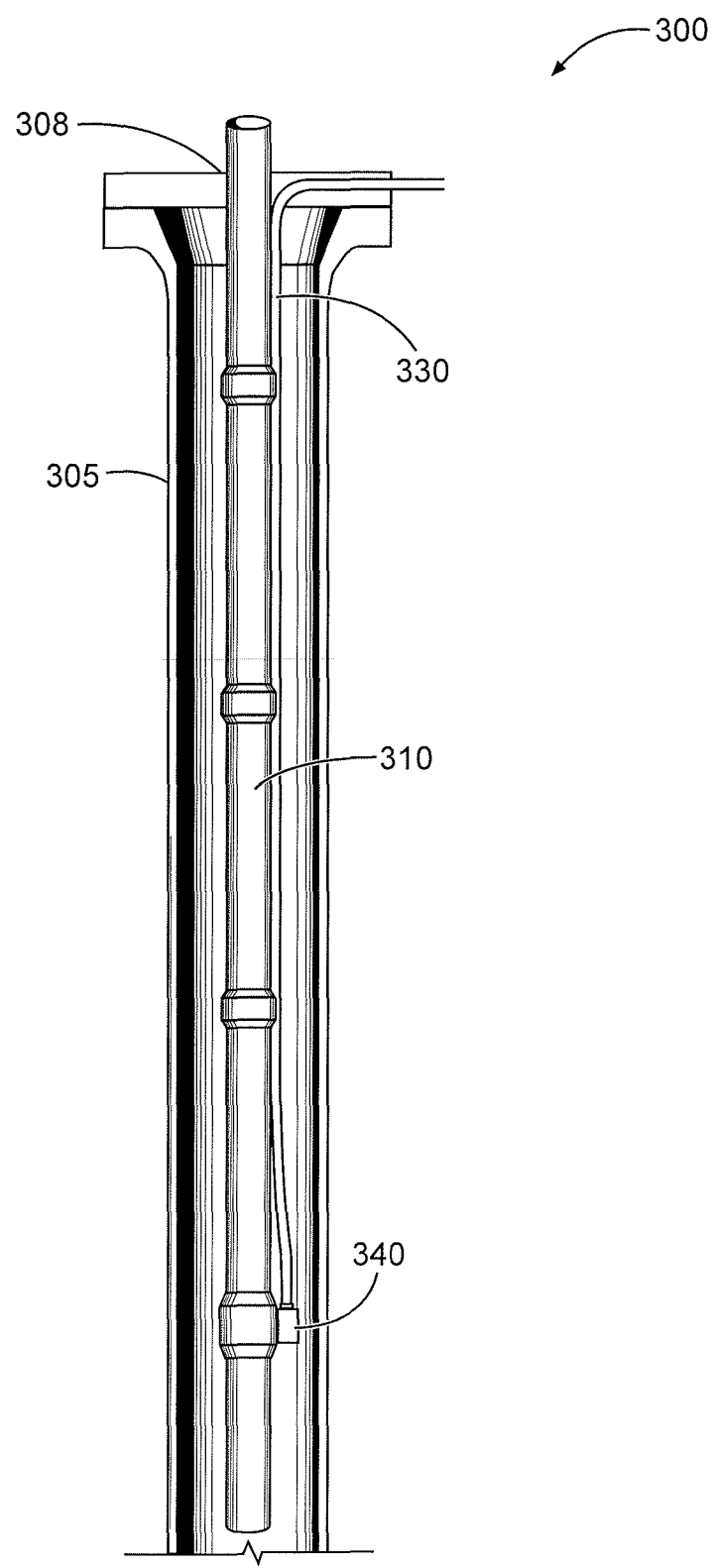
FIG. 3 is a diagram illustrating an injection system used in accordance with certain embodiments of the present disclosure.

For example, a LDHI additive of the present disclosure may be introduced into a wellbore and/or tubing using a capillary injection system as shown in FIG. 3. Referring now to FIG. 3, wellbore 305 has been drilled to penetrate a portion of a subterranean formation 300. A tubing 310 (e.g., production tubing) has been placed in the wellbore 305. A capillary injection tube 330 is disposed in the annular space between the outer surface of tubing 310 and the inner wall of wellbore 305. The capillary injection tube 330 is connected to a side-pocket mandrel 340 at a lower section of the tubing 310. A LDHI additive of the present disclosure may be injected into capillary injection tube 330 at the wellhead 308 at the surface such that it mixes with production fluid at or near the side-pocket mandrel 340. As the production fluid flows through the tubing 310, the LDHI additive may prevent, inhibit, retard, reduce, control, and/or delay the formation of one or more hydrates within the tubing 310. Other capillary injection systems and side pocket mandrel devices (e.g., those used in gas lift production) may be used in a similar manner to the system shown in FIG. 3.

In certain embodiments, a LDHI additive of the present disclosure may be added to a conduit such as a pipeline where one or more fluids enter the conduit and/or at one or more other locations along the length of the conduit. In such embodiments, the LDHI additive may be added in batches or injected substantially continuously while the pipeline is being used.

Once introduced into a fluid, subterranean formation, wellbore, pipeline, or other location, the LDHI additive may inhibit, retard, reduce, control, and/or delay the formation of one or more hydrates or the agglomeration of hydrate crystals within the fluid, subterranean formation, wellbore, pipeline, or other location.

To facilitate a better understanding of the present disclosure, the following examples of certain aspects of certain embodiments are given. The following examples are not the only examples that could be given according to the present disclosure and are not intended to limit the scope of the disclosure or claims.

EXAMPLES

Rocking cell tests were carried out on several samples comprising different LDHI additives having structures according to some embodiments of the present disclosure. Rocking cell tests involve injection of gas, oil, water, and an LDHI additive into a cell at representative conditions. Optionally, additional gas may be injected into the cell (e.g., to achieve a desired working pressure during the experiment). Each cell was of a fixed volume and contained constant mass during the experiment; that is, oil, water, an LDHI additive, and gas were injected at the beginning of the experiment, but thereafter the cell was closed to mass transfer in or out of the cell. Each cell also included a magnetic ball in the space where fluids are injected. The ball aided in agitation of the fluids during rocking. In addition, magnetic sensors on both ends of the cell detected whether the magnetic ball's movements through the fluids were hindered during rocking, wherein such hindrance could indicate the presence of hydrates. The cell also permitted visual observation of its contents during the experiment.

Initially, amounts of oil, water, and an LDHI additive were injected into the cell so as to achieve the desired water cut (i.e., fraction of aqueous phase in the total fluid) and LDHI additive dosage (volume % of LDHI additive on water cut basis) of the experiment. After injection of oil, water, and LDHI additive, gas was injected to reach a desired pressure (e.g., working pressure of a conduit of interest for evaluation of the LDHI additive, in this case around 2,800 psi). Gas composition varied based upon the conditions that would be encountered in the target conduit for the LDHI additive.

Following injection of the gas, the cell was closed and rocked for approximately 2 hours to emulsify the fluids therein. The temperature was then ramped down from about 20° C. to about 4° C. over a period of about 1 hour, and rocking was continued for around 16 hours after the temperature reached about 4° C. The rocking was then stopped for a period of time while the cell is horizontal (e.g., to simulate a system shut-in). This "shut-in" period lasts for at least 6 hours, varying only so that the re-start of rocking could be visually observed.

Visual inspection of the contents of the cell was made throughout the tests for visual rating of the performance of the LDHI additive as a hydrate inhibitor. Visual rating results in a score based upon a scale of 1 through 5 according to the criteria set forth in Table 1 below. Samples that obtain a score of 4 or 5 pass the visual inspection while samples that obtain a score of 1-3 fail.

TABLE 1

Rocking Cell Visual Rating Criteria for LDHI Additives

| Grade | Description |
| --- | --- |
| 5 | No or Ultra-Fine Hydrate Crystals; Fully Flowable System |
| 4 | Larger Hydrate Particles and/or More Viscous Liquid than Grade 5; Flowable System |
| 3 | System will Flow with Difficulty |
| 2 | System will Most Likely Plug |
| 1 | System will Plug |

Example 1

Samples were prepared including LDHI additives of the present disclosure—LDHI 1, LDHI 2, and LDHI 3—as well as commercially available LDHI additives of the prior art—Product A and Product B. The LDHI additives of the present disclosure had the following base structure:

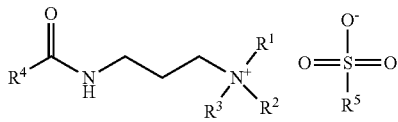

The $R^1$, $R^2$, $R^3$, $R^4$, and $R^5$ groups for each LDHI additive of the present disclosure are defined below in Table 2. The commercially available LDHI additives of the prior art were Product A, a quaternary ammonium salt, and Product B, a tertiary ammonium salt.

TABLE 2

LDHI Additives with Salinized Water

| LDHI Additive | $R^1/R^2$ | $R^3$ | $R^4$ | $R^5$ | Dose | 50% Water Cut | 55% Water Cut | 60% Water Cut |
| --- | --- | --- | --- | --- | --- | --- | --- | --- |
| Product A | | | | | 2% | Passed | Passed | Failed |
| Product B | | | | | 2% | Passed | Passed | Passed |
| LDHI 1 | $C_4H_9$ | H | Coconut oil | $CH_3$ | 2% | Passed | Passed | Passed |
| LDHI 2 | $C_4H_9$ | $C_2H_5$ | Coconut oil | $CH_2CH_3$ | 2% | Passed | Passed | Passed |
| LDHI 3 | $C_4H_9$ | H | $C_{11}H_{23}$ | $CH_3$ | 2% | Passed | Passed | Passed |

As also indicated in Table 2, each LDHI additive was applied at the indicated dosage (2.0% v/v based on water cut) to fluids having three different water cuts: 50%, 55%, and 60%. The water in each sample had a salinity of 6% total dissolved solids. As shown by the results in Table 2, each LDHI additive of the present disclosure—LDHI 1, LDHI 2, and LDHI 3—passed at each water cut and performed better than at least one LDHI additive of the prior art at a water cut of 60%. Thus, Example 1 demonstrates that the compositions and methods of the present disclosure may facilitate, among other benefits, the inhibition, retardation, reduction, control, and/or delay of agglomeration of hydrates and/or hydrate-forming compounds in fluids having a water cut of about 60% or greater.

Example 2

Samples were prepared including a LDHI additive of the present disclosure LDHI 1—as well as commercially available LDHI additives of the prior art—Product C and Product B. The LDHI additives of the present disclosure had the following base structure:

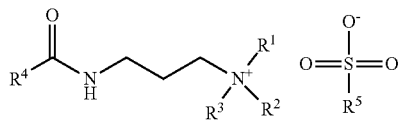

The $R^1$, $R^2$, $R^3$, $R^4$, and $R^5$ groups for the LDHI additive of the present disclosure are defined below in Table 3. The commercially available LDHI additives of the prior art were Product B, a tertiary ammonium salt, and Product C, a tertiary ammonium salt.

TABLE 3

LDHI Additives with Deionized Water and Thermal Aging

| LDHI Additive | $R^1/R^2$ | $R^3$ | $R^4$ | $R^5$ | Dose | 10% Water Cut | 15% Water Cut |
| --- | --- | --- | --- | --- | --- | --- | --- |
| Product B | | | | | 5% | Failed | Failed |
| Product C | | | | | 5% | Failed | Failed |
| LDHI 1 | $C_4H_9$ | H | Coconut fatty acid | $CH_3$ | 5% | Passed | Passed |

As also shown in Table 3, each LDHI additive was applied at the indicated dosage (5% v/v based on water cut) to fluids having two different water cuts: 10% and 15%. Deionized water was used in each sample. The samples were aged for 24 hours at 300° F. before performing the visual inspection. As shown by the results in Table 3, LDHI 1 of the present disclosure passed at each water cut and performed better than both LDHI additives of the prior art at both water cuts. Thus, Example 2 demonstrates that the compositions and methods of the present disclosure may facilitate, among other benefits, the inhibition, retardation, reduction, control, and/or delay of agglomeration of hydrates and/or hydrate-forming compounds in fluids comprising deionized water and/or at temperature of at least about 300° F.

Example 3

An initial FTIR spectrum was taken of LDHI 1 from Example 2 and Product B. The LDHI additives were then aged for 7 days at 250° F. and a final FTIR spectrum was taken of each LDHI additives. The correlation coefficient between the initial and final spectra of the LDHI 1 was 98.74%, indicating the absence of substantial degradation of the LDHI additive of the present disclosure. The correlation coefficient of the initial and final spectra of Product B was 71.55%, indicating substantial degradation of the LDHI additive of the prior art. Thus, Example 3 demonstrates that the compositions and methods of the present disclosure may facilitate, among other benefits, the inhibition, retardation, reduction, control, and/or delay of agglomeration of hydrates and/or hydrate-forming compounds in fluids after being substantially continually exposed to a temperature of at least about 250° F. for up to about 7 days without substantially degrading.

An embodiment of the present disclosure is a method comprising: introducing a low-dosage hydrate inhibitor additive into a fluid comprising water and at least one component selected from the group of: a gas, a liquid hydrocarbon, and any combination thereof, wherein the low-dosage hydrate inhibitor additive comprises at least one compound having the structural formula:

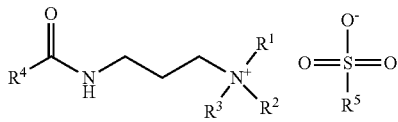

wherein each of $R^1$ and $R^2$ is independently a $C_1$ to $C_6$ hydrocarbon chain, wherein $R^3$ is selected from the group consisting of hydrogen and a $C_1$ to $C_6$ hydrocarbon chain, wherein $R^4$ is a $C_1$ to $C_{50}$ hydrocarbon chain, and wherein $R^5$ is an organic moiety; and exposing the low-dosage hydrate inhibitor additive to a temperature above about 200° F.

Another embodiment of the present disclosure is a method comprising: introducing a low-dosage hydrate inhibitor additive into a wellhead of a wellbore penetrating at least a portion of a subterranean formation having a temperature above about 200° F., wherein the low-dosage hydrate inhibitor additive comprises at least one compound having the structural formula:

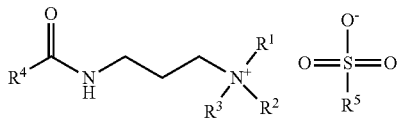

wherein each of $R^1$ and $R^2$ is independently a $C_1$ to $C_6$ hydrocarbon chain, wherein $R^3$ is selected from the group consisting of hydrogen and a $C_1$ to $C_6$ hydrocarbon chain, wherein $R^4$ is a $C_1$ to $C_{50}$ hydrocarbon chain, and wherein $R^5$ is an organic moiety; and allowing the low-dosage hydrate inhibitor additive to contact a fluid in the wellbore.

Another embodiment of the present disclosure is a method comprising: introducing a low-dosage hydrate inhibitor additive into a conduit having a temperature above about 200° F. and containing a fluid, wherein the low-dosage hydrate inhibitor additive comprises at least one compound having the structural formula:

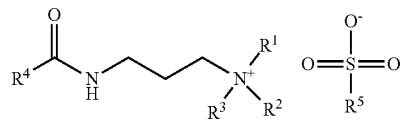

wherein each of $R^1$ and $R^2$ is independently a $C_1$ to $C_6$ hydrocarbon chain, wherein $R^3$ is selected from the group consisting of hydrogen and a $C_1$ to $C_6$ hydrocarbon chain, wherein $R^4$ is a $C_1$ to $C_{50}$ hydrocarbon chain, and wherein $R^5$ is an organic moiety.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. While numerous changes may be made by those skilled in the art, such changes are encompassed within the spirit of the subject matter defined by the appended claims. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. In particular, every range of values (e.g., "from about a to about b," or, equivalently, "from approximately a to b," or, equivalently, "from approximately a-b") disclosed herein is to be understood as referring to the power set (the set of all subsets) of the respective range of values. The terms in the claims have their plain, ordinary meaning unless otherwise explicitly and clearly defined by the patentee.

What is claimed is:
1. A method comprising:
introducing a low-dosage hydrate inhibitor additive into a fluid, wherein the low-dosage hydrate inhibitor additive comprises at least one compound having the structural formula:

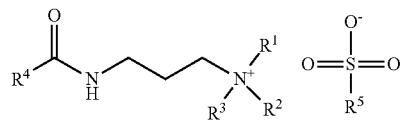

wherein each of $R^1$ and $R^2$ is independently a $C_1$ to $C_6$ hydrocarbon chain,
wherein $R^3$ is selected from the group consisting of hydrogen and a $C_1$ to $C_6$ hydrocarbon chain,
wherein $R^4$ is a $C_1$ to $C_{50}$ hydrocarbon chain, and
wherein $R^5$ is an organic moiety; and
exposing the low-dosage hydrate inhibitor additive to at least one temperature above about 200° F., wherein the low-dosage hydrate inhibitor additive does not substantially degrade for up to about 7 days after being substantially continually exposed to at least one temperature of above about 200° F.

2. The method of claim 1 wherein the organic moiety is selected from the group consisting of: an alkyl group, an alkenyl group, an aryl group, an arylalkyl group, an arylalkenyl group, an alkylaryl group, an alkenylaryl group, a heterocyclic group, a hydroxyl group, a carbonyl group, an amine group, and any combination thereof.

3. The method of claim 1 wherein the fluid comprises at least one component selected from the group consisting of: water, a gas, a liquid hydrocarbon, and any combination thereof.

4. The method of claim 1 wherein the low-dosage hydrate inhibitor additive is introduced into a quaternary ammonium cation moiety or a tertiary ammonium cation moiety the fluid through a conduit or an injection point having at least one temperature above about 200° F. and the low-dosage hydrate inhibitor additive is exposed to at least one temperature above about 200° F. in the conduit or the injection point.

5. The method of claim 1 wherein the fluid has at least one temperature above about 200° F. and the low-dosage hydrate inhibitor additive is exposed to at least one temperature above about 200° F. in the fluid.

6. The method of claim 1 wherein the fluid resides within a location selected from the group consisting of: a conduit, a wellbore, a subterranean formation, and a vessel.

7. The method of claim 1 wherein the fluid comprises water and has a water cut of from about 1% to about 65%.

8. The method of claim 1 wherein the fluid comprises water and has a water cut of about 50% or greater.

9. The method of claim 1 wherein the low-dosage hydrate inhibitor additive is introduced in an amount such that the low-dosage hydrate inhibitor additive is present in the fluid in an amount from about 0.1% to about 10% volume based on the water cut of the fluid.

10. The method of claim 1 wherein the water is selected from the group consisting of: brine, deionized water, and any combination thereof.

11. A method comprising:
introducing a low-dosage hydrate inhibitor additive into a wellhead of a wellbore penetrating at least a portion of a subterranean formation having at least one temperature above about 200° F., wherein the low-dosage hydrate inhibitor additive does not substantially degrade for up to about 7 days after being substantially continually exposed to at least one temperature of above about 200° F., wherein the low-dosage hydrate inhibitor additive comprises at least one compound having the structural formula:

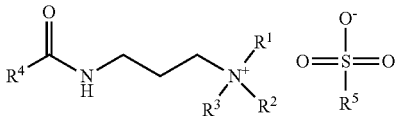

wherein each of $R^1$ and $R^2$ is independently a $C_1$ to $C_6$ hydrocarbon chain,
wherein $R^3$ is selected from the group consisting of hydrogen and a $C_1$ to $C_6$ hydrocarbon chain,
wherein $R^4$ is a $C_1$ to $C_{50}$ hydrocarbon chain, and
wherein $R^5$ is an organic moiety; and
allowing the low-dosage hydrate inhibitor additive to contact a fluid in the wellbore.

12. The method of claim 11 wherein the fluid comprises at least one component selected from the group consisting of: water, a gas, a liquid hydrocarbon, and any combination thereof.

13. The method of claim 11 wherein the fluid comprises water and has a water cut of about 50% or greater.

14. The method of claim 11 wherein wellbore has at least one temperature from about 250° F. to about 350° F.

15. A method comprising:
introducing a low-dosage hydrate inhibitor additive into a conduit having at least one temperature above about 200° F. and containing a fluid, wherein the low-dosage hydrate inhibitor additive does not substantially degrade for up to about 7 days after being substantially continually exposed to at least one temperature of above about 200° F., wherein the low-dosage hydrate inhibitor additive comprises at least one compound having the structural formula:

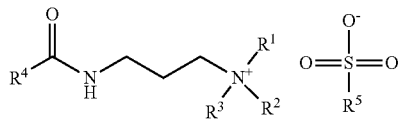

wherein each of $R^1$ and $R^2$ is independently a $C_1$ to $C_6$ hydrocarbon chain,
wherein $R^3$ is selected from the group consisting of hydrogen and a $C_1$ to $C_6$ hydrocarbon chain,
wherein $R^4$ is a $C_1$ to $C_{50}$ hydrocarbon chain, and
wherein $R^5$ is an organic moiety.

16. The method of claim 15 wherein the fluid comprises at least one component selected from the group consisting of: water, a gas, a liquid hydrocarbon, and any combination thereof.

17. The method of claim 15 wherein the conduit has at least one temperature from about 250° F. to about 350° F.

* * * * *